Figure 3:
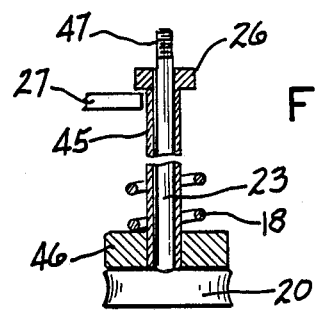

United States Patent [19]

Lucas

[11] Patent Number: 4,738,660
[45] Date of Patent: Apr. 19, 1988

[54] INJECTION SYRINGE

[76] Inventor: Dieter Lucas, Schlossstrasse 5, D-7763 Öhningen-Kattenhorn, Fed. Rep. of Germany

[21] Appl. No.: 834,329
[22] PCT Filed: May 8, 1985
[86] PCT No.: PCT/DE85/00149
    § 371 Date: Mar. 10, 1986
    § 102(e) Date: Mar. 10, 1986
[87] PCT Pub. No.: WO85/05275
    PCT Pub. Date: Dec. 5, 1985

[30] Foreign Application Priority Data

May 12, 1984 [DE] Fed. Rep. of Germany ....... 3417757

[51] Int. Cl.$^4$ .............................................. A61M 5/00
[52] U.S. Cl. ..................... 604/139; 604/205; 604/191; 604/157
[58] Field of Search ............... 604/136, 139, 138, 157, 604/191, 201, 202, 205, 206

[56] References Cited

U.S. PATENT DOCUMENTS

| | | |
|---|---|---|
| 1,561,854 | 8/1924 | Hein . |
| 4,040,420 | 8/1977 | Speer . |
| 4,109,653 | 8/1978 | Kozam . |
| 4,178,928 | 12/1979 | Tischlingler ................. 604/205 X |
| 4,359,049 | 11/1982 | Redl et al. . |

FOREIGN PATENT DOCUMENTS

| | | |
|---|---|---|
| 0024046 | 2/1981 | European Pat. Off. . |
| 0037393 | 4/1981 | European Pat. Off. . |
| 208720 | 2/1907 | Fed. Rep. of Germany . |
| 1491877 | 5/1969 | Fed. Rep. of Germany . |
| 2533594 | 2/1976 | Fed. Rep. of Germany . |
| 1051010 | 1/1954 | France . |
| 1054173 | 2/1954 | France . |
| 1116922 | 5/1956 | France . |
| 2191912 | 2/1974 | France . |

Primary Examiner—Stephen C. Pellegrino
Attorney, Agent, or Firm—Bachman & LaPointe

[57] ABSTRACT

An injection syringe having at least two chambers which are disposed in axis-parallel and juxtaposed relationship and an injection needle in which the needle cavity can be connected to a chamber for an injection liquid which can be pressurized by an injection piston that can be put under load, is intended to provide a syringe construction which is simplified in comparison with the state of the art, for manual handling of the injection piston, as well as mixing of a plurality of injection liquids during the injection operation. For that purpose, the juxtaposed chambers are each provided with an injection piston and communicate with a common prechamber which is formed by a releasable cap carrying the injection needle.

11 Claims, 2 Drawing Sheets

U.S. Patent   Apr. 19, 1988   Sheet 1 of 2   4,738,660

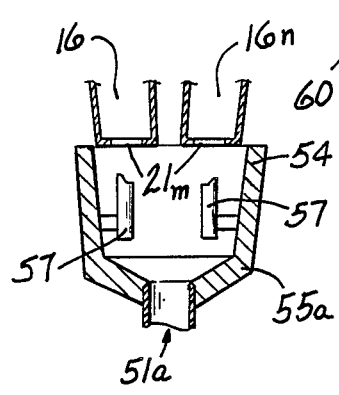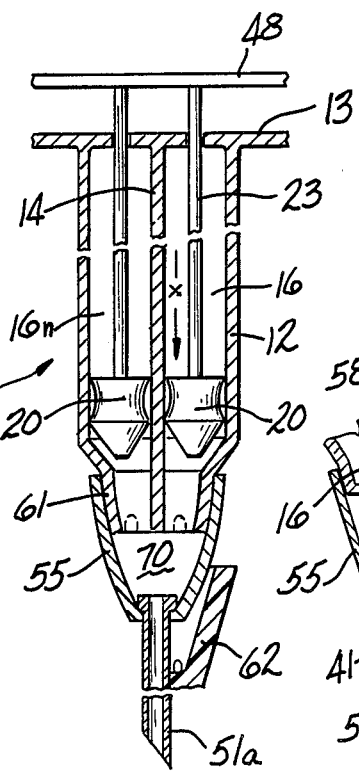

INJECTION SYRINGE

The invention relates on the one hand to an injection syringe having at least two chambers which are disposed in juxtaposed and axis-parallel relationship, and an injection needle whose needle cavity can be connected to a chamber for an injection liquid which can be put under pressure by a syringe piston which can be put under load, and on the other hand to an injection syringe having an injection needle which can be pushed out of a needle chamber from a readiness position into an operative position by a force storage means, and a closed container which is disposed in axis-parallel relationship with the needle chamber and which accommodates an injection fluid that can be put under pressure by a syringe piston which can be put under load, the injection needle of the syringe, which has a needle duct, being connected in the operative position to a liquid chamber of the container.

In his patent application No. P 29 32 719.3 the inventor put forward an injection syringe of that kind, with which it is possible for the time delay between the operation of pushing out the injection needle and the beginning of the injection to be longer than in the case of known syringes. With the previously known needle, that is achieved in that the needle chamber and the container extend in axis-parallel relationship, and that the injection needle is connected by way of a lateral opening associated therewith, and an outlet aligned therewith in the operative position in a wall of the liquid container, wherein the syringe piston for pressurising the liquid and the needle piston are released by a lift means which delays the release of the syringe piston with respect to the needle piston.

A further improvement in such injection syringes is intended to permit a simplification in the syringe structure, selectively also manual operation of the syringe piston, and mixing of a plurality of syringe liquids during the injection process.

That object is attained in that the juxtaposed chambers are each provided with a syringe or injection piston and communicate with a common prechamber which is formed by a releasable cap carrying the injection needle.

It is also in accordance with the invention that the juxtaposed chaxbers are respectively provided with a syringe or injection piston and are provided at one end with a ccmmon cap carrying the injection needle, wherein the injection needle, in the inside of the cap, has a number of contact ends, said number corresponding to the number of chambers, which contact ends can be applied against bottom portions of the injection syringe and can be pushed thereinto by means of the cap.

That arrangement which is further supplemented by the features set forth in the subsidiary claims provides a very simple syringe instrument which achieves the object envisaged.

In accordance with the invention, another way of achieving the object of the invention provides that the liquid chamber has a projection portion or formation which projects towards the needle chamber and into which a pin-like part of the injection needle extends in the operative position; in accordance with the invention same is to be of a U-shaped configuration, with a long limb as the injection tip and with a short limb as the pinlike part; the entire injection needle is provided with the needle duct extending therethrough.

An essential aspect in regard to the injection syringe according to the invention is the stop lever which is described in German laid-open application (DE-OS) No 29 32 719 and which is formed for example as a rocker member.

The stop lever makes it possible for firstly the injection needle to be set in motion and for the injection piston to be moved only when the injection needle has reached its operative position.

It is also in accordance with the invention that resting on the syringe piston is a pressure plate or a corresponding piston disc with axial piston barrel in which an externally accessible piston rod of the injection piston is displaceably mounted and which is held by a stop member in the readiness position. That makes it possible for the injection piston itself to be connected to a handle means while its pressure members, a coil spring and each pressure plate, are connected to the stop lever and controlled thereby.

Of particular advantage is an arrangement of a plurality of containers around a common, preferably centrally disposed needle chamber, wherein each of said containers is provided with said projection portion or formation and can be opened by a pin-like part of a common injection needle. That permits the simultaneous use of a plurality of injection liquids which flow together during the injection operation. If the piston rods of the needle pistons are connected by a common pressure yoke member or a corresponding handle or operating means, that ensures synchronous actuation of all injection pistons.

An important aspect of the present invention is a desiredrupture location in the upper region of the projection portion or formation, which forms a secondary chamber, in the liquid chamber, being for example in the form of a skin or membrane; it is disposed in the path of movement of the shorter limb of the injection syringe and is ruptured thereby when it is under a spring loading.

In an arrangement comprising a plurality of liquid chambers around a common needle chamber, in accordance with the invention the injection needle is provided in an upward direction with a plurality of pin-like limbs which there form a kind of tubular crown and extend in mutually parallel relationship.

For the purposes of guiding the injection nozzle, it has also been found to be advantageous for at least one outside surface of said secondary chambers to represent a guide means for the injection needle; in an arrangement comprising a plurality of secondary chambers, the injection needle may be satisfactorily held between them.

Particularly important in regard to operational security and reliability of the injection syringe according to the invention is the feature that provided in the needle chamber is at least one stop member which holds the needle piston in the operative position of the injection needle. A preferred embodiment of that stop member is a flexible lip which serves as an abutment in the opposite direction to the direction of extension of the injection needle; when the injection needle is extended into its operative position, said lip yields and then stands up above the needle piston as a support means.

Other stop members also lie within the scope of the invention, insofar as they perform the above-described function.

Figure 1:
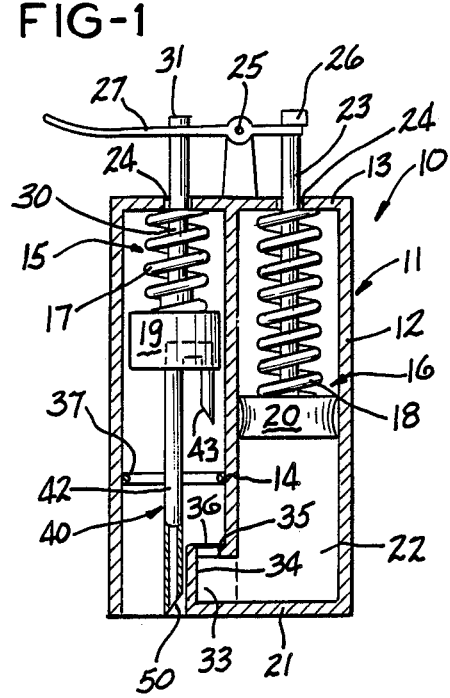
Figure 5:
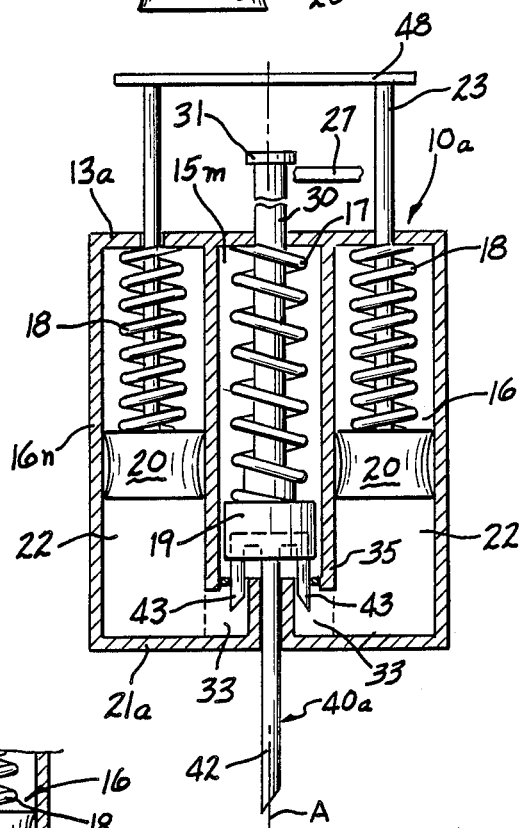
Figure 4:
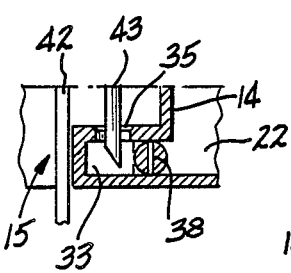
Figure 2:
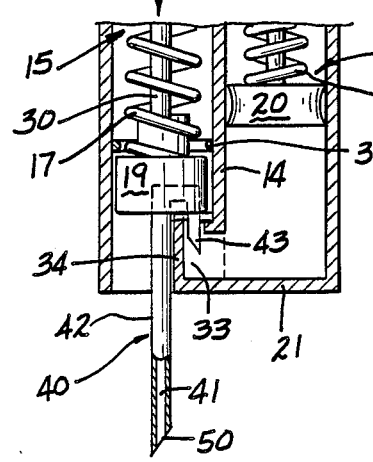

Further advantages, features and details of the invention will be apparent from the following description of preferred embodiments and with reference to the drawings which each show views in longitudinal section and in which:

FIG. 1 illustrates an injection syringe having two chambers which are disposed in mutually juxtaposed and parallel relationship and an injection needle in the readiness position, FIG. 2 shows a part of the injection syringe of FIG. 1, with the injection needle in the operative position, FIG. 3 shows a view on an enlarged scale of a detail from FIG. 1, in relation to a further embodiment, FIG. 4 shows another detail from FIG. 1, in a modified embodiment, FIG. 5 shows an injection syringe having a plurality of chambers around a central injection needle, FIG. 6 shows a detail of an injection needle, FIG. 7 shows a detail corresponding to the view shown in FIG. 5, of another embodiment, and FIG. 8 shows another embodiment of an injection syringe with a plurality of juxtaposed chambers.

Referring to FIG. 1, an injection syringe 10 comprises, in a housing 11 having side walls 12 and a cover or top plate portion 13, a container 16 which is disposed in axis-parallel relationship and which is separated from a needle chamber 15 by a central wall portion 14. Disposed in the needle chamber 15 and the container 16 are respective coil springs 17 and 18 respectively which on the one hand bear against the cover or top plate portion 13 and on the other hand are respectively connected to a needle piston 19 and a syringe or injection piston 20.

The injection piston 20, in the container 16 which extends at the right in FIG. 1, defines, together with a bottom plate portion 21, a liquid chamber 22 for an injection liquid which is not shown in the drawings for the sake of simplicity thereof. The injection piston 20 is fixed to a piston rod 23 which passes through an opening 24 in the cover or top plate portion 13, and is held by a stop lever 27 which is mounted pivotably at 25 and which engages under a head portion 26 on the piston rod.

A corresponding piston rod 30 extends from the needle piston 16 of the needle chamber 15 and is held in the stop position by its head portion 31, at the above-mentioned stop lever 27.

An injection needle 40 of a U-shaped configuration, with a needle duct 41 extending therethrough, is fixed to or integrated into the needle piston 19.

When the piston rod 30 is released, the needle piston 19 moves downwardly and therewith the injection needle 40 secured thereto, into their operative position as shown in FIG. 2. A long limb 42 of the injection needle 40 extends out of the downwardly open needle chamber 15 while the short limb 43 extends into a secondary chamber 33 of the liquid chamber 22 which is on the right. The secondary chamber 33 adjoins the bottom plate portion 21 and has its wall portion 34 extending into the needle chamber 15 to such a distance that the wall portion 34 affords a guide means for the long limb 42 of the injection needle 40.

The cover or top portion of the secondary chamber 33 is provided with an opening 36 which is closed by a skin or membrane 35. When the injection needle 40 is moved downwardly, the skin or membrane 35 can be easily ruptured or pierced by the short limb 42 of the injection needle 40. After the injection needle 40 has been set in position, the piston rod 23 is released from the stop lever 27 whereby the injection liquid is ejected.

When the injection needle 40 moves downwardly, the needle piston 19 slides through a lip ring 37, in the direction of extension as indicated by x. In the operative position, the lip ring 37 engages over the needle piston 19 to act as a support means or abutment. The abutment means 37 may also be of a different configuration but it must permit the downward movement of the needle piston 19 and must perform the function of the support means.

By virtue of the particular configuration of the injection syringe, a suction effect can be produced, that is to say a reduced pressure or depression can be generated, when the stop lever 27 is lifted up, or depressed.

In FIG. 3, the piston rod 23 extends in a piston tube or barrel 45 which at one end is carried with a piston disk 46 on the piston 20 and which at the other end carries the head portion 26 of the piston rod; the piston rod 23 is displaceable in the piston barrel or tube 45 and is provided with a terminal screwthread portion 47 for connection to a handle (not shown). Here the force of the coil spring 18 is arrested by the horizontally divided, doubled piston 20/46.

As the piston rod 23 of the syringe or injection piston 20 is movable in the piston barrel 45, an injection operation can also be permitted only by virtue of using manual pressure. The handle which is then fitted to the arrangement is used for that purpose.

In the embodiment of FIG. 4, the secondary chamber 33 is separated from the liquid chamber 22 by a valve 38; the path for the liquid to the injection nozzle 40 is opened by intentional actuation of the valve 38. The valve 38 thus permits quantitative control or metering of the injection material or liquid.

The injection syringe $10_a$ as shown in FIG. 5 comprises a plurality of containers or injection material chambers 16 through $16_n$ which are arranged around a central needle chamber $15_m$ and which are provided with common cover and bottom plate portions $13_a$ and $21_a$, as well as a common pressure yoke member 48 for their piston rods 23. The injection needle $40_a$ which extends along the axis A of the syringe has a plurality of short limbs 43, the number thereof corresponding to the number of chambers 16 through $16_n$. The limbs 43 are disposed in a crown-like array around the long central limb 42, and the needle ducts thereof communicate with the central needle duct 41 of the long limb 42.

After the skins or membranes 35 are pierced by means of the bevelled needle cutting edges 50, a plurality of chambers 16, $16_n$ are opened, which permits the liquids therein to be mixed during the injection operation. In addition the common pressure yoke member 48 ensures uniform mixing or dilution of the various substances in the chambers.

FIGS. 6 and 7 show parts of injection syringes 58 having a plurality of injection material chambers 16 through $16_n$ and particular shapes of the injection needle 51 and $51_a$ respectively, with a plurality of upwardly directed inlets 52. In FIG. 6, the form of the needle head portion 53 is similar to a fork or a three-prong member. The above-mentioned inlets 52 are intended to pierce bottom portions $21_m$ and to provide a communication by way of the injection syringe and give a discharge flow. The injection needle 51 is disposed in a cap 55 which is pushed on a collar portion 71 of a multi-chamber syringe 58. Shown between the containers 16, $16_n$ thereof is a slot 59 in which the central wall portion 56 of the cap 55 is movable when the cap 55 is pushed on to the syringe. The space 70 inside the cap serves as a syringe or injection prechamber.

Referring to FIG. 7, a cap $55_a$ of a different construction is associated with the bottom portion $21_m$, with a cutting tube 57 which is fixed to the wall portion 54 of the cap $55_a$, for opening the injection material chambers 16, $16_n$ when the cap $55_a$ is lifted.

The multi-chamber syringe 60 shown in FIG. 2 also has a cap 55 in which an injection needle 71 is carried and which is pushed on to an end portion 61 of the syringe. Before the cap 55 is pushed on to the syringe, the end portion 61 of the syringe is provided with a closure cap 62 which is only indicated in FIG. 7.

The end portion 61 of the syringe is reduced or tapered in comparison with the containers 16, $16_n$ which are disposed upstream thereof in the direction of injection as indicated by x. The piston rods 23 which are connected by means of a pressure yoke member 48 permit an increased pressure to be applied.

I claim:

1. An injection syringe comprising: a housing having a needle chamber and at least one liquid storage chamber arranged parallel to each other; an injection needle movably mounted in said needle chamber from a first readiness position to a second operative position, said injection needle being provided with means for communicating with said liquid storage chamber when said injection needle is in said second operative position; and piston means mounted in said liquid storage chamber for putting liquid in said liquid storage chamber under pressure such that liquid passes from said liquid storage chamber through said means for communicating when said injection needle is in said second operative position wherein the portion of said liquid storage chamber projects under said needle chamber for forming a secondary chamber which receives said communicating means of said injection needle.

2. A syringe according to claim 1 including a plurality of liquid storage chambers arranged about said needle chamber wherein said injection needle is provided with a plurality of communicating means which communicate with said plurality of liquid storage chambers when said injection needle is in said second operative position.

3. A syringe according to claim 1 wherein a valve is provided between said liquid storage chamber and said secondary chamber for controlling the flow of liquid therebetween.

4. A syringe according to claim 1 wherein said piston connected to a piston rod which projects out of said liquid storage chamber.

5. A syringe according to claim 1 wherein said means for communicating comprises a short limb and wherein said injection needle further comprises a long limb substantially parallel to said short limb and connected by a base portion to said short limb so as to form a substantially U-shaped configuration wherein said short limb communicates with said secondary chamber of said liquid storage chamber when said injection needle is in said second operative position.

6. A syringe according to claim 5 wherein a ruptural membrane separates said secondary chamber from said needle chamber wherein said communicating means punctures said membrane when said injection needle is in said second operation position.

7. A syringe according to claim 6 wherein said short limb is provided with cutting means on the end thereof for puncturing said membrane.

8. A syringe according to claim 5 wherein said injection needle is carried by a piston which is reciprocally mounted in said needle chamber by a piston rod which projects out of said needle chamber.

9. A syringe according to claim 1 wherein a ruptural membrane separates said secondary chamber from said needle chamber wherein said communicating means punctures said membrane when said injection needle is in said second operation position.

10. A syringe according to claim 1 wherein the needle chamber is provided with at least one stop member for holding said injection needle in said second operative position.

11. A syringe according to claim 10 wherein said at least one stop member comprises a flexible lip.

* * * * *